(12) United States Patent
Chen et al.

(10) Patent No.: US 6,834,547 B2
(45) Date of Patent: Dec. 28, 2004

(54) HUMIDITY SENSOR AND FABRICATION METHOD THEREOF

(75) Inventors: Chih-Kun Chen, Taoyuan (TW); Yao-Hsiung Kung, Taoyuan (TW); Chung-Min Lin, Taipei (TW); Hsin-Chuan Tsai, Taipei (TW)

(73) Assignee: Nanya Technology Corporation, Taoyuan (TW)

( * ) Notice: Subject to any disclaimer, the term of this patent is extended or adjusted under 35 U.S.C. 154(b) by 0 days.

(21) Appl. No.: 10/440,934

(22) Filed: May 19, 2003

(65) Prior Publication Data

US 2004/0040378 A1 Mar. 4, 2004

(30) Foreign Application Priority Data

Aug. 28, 2002 (TW) .................................. 91119512 A

(51) Int. Cl.$^7$ ............................ G01N 1/00; G01N 19/00
(52) U.S. Cl. .................................. 73/335.02; 73/29.05
(58) Field of Search ........................ 73/29.01, 335.02, 73/335.03, 335.04, 335.05, 29.05

(56) References Cited

U.S. PATENT DOCUMENTS

| 4,144,636 | A | * | 3/1979 | Burkhardt et al. | 438/49 |
| 4,642,601 | A | * | 2/1987 | Sugawara et al. | 338/35 |
| 4,684,884 | A | * | 8/1987 | Soderlund | 324/71.1 |
| 5,216,226 | A | * | 6/1993 | Miyoshi | 219/497 |
| 6,445,565 | B1 | * | 9/2002 | Toyoda et al. | 361/303 |

FOREIGN PATENT DOCUMENTS

| DE | 2517088 | * | 3/1976 | ................ 73/29.05 |

* cited by examiner

*Primary Examiner*—Daniel S. Larkin
(74) *Attorney, Agent, or Firm*—Quintero Law Office

(57) ABSTRACT

A humidity sensor and fabrication method thereof. In the humidity sensor of the present invention, two comb-type electrodes with a plurality of teeth are disposed on a semiconductor substrate. A $SiO_2$ sensing film is disposed between the teeth of the two comb-type electrodes on the substrate. A predetermined voltage is applied between the two comb-type electrodes, a leakage current between the two electrodes is detected, and the humidity in the environment is measured according thereto.

11 Claims, 7 Drawing Sheets

HUMIDITY SENSOR AND FABRICATION METHOD THEREOF

BACKGROUND OF THE INVENTION

1. Field of the Invention

The present invention relates to a sensor, and in particular to a humidity sensor, its detection method, and fabrication thereof.

2. Description of the Related Art

Conventionally, humidity sensors detect humidity in an environment and are generally used in air conditioning systems, dehumidifiers, dryers, and the like. Such wide use requires the humidity sensors to provide dependable operation.

Consequently, the humidity sensors can be mass produced at low cost if utilizing semiconductor process together with a simple structure and process, and lower material consumption.

SUMMARY OF THE INVENTION

Accordingly, an object of the invention is to provide a humidity sensor with a simple structure, its method of detection, and fabrication method thereof.

Another object of the invention is to provide a method for detecting the humidity in the environment.

According to the above mentioned objects, the present invention provides a humidity sensor. In the humidity sensor of the present invention, two comb-type electrodes with a plurality of teeth are disposed on a semiconductor substrate. A $SiO_2$ sensing film is disposed between the teeth of the two comb-type electrodes on the substrate. A predetermined voltage is applied between the two comb-type electrodes, leakage current between the two electrodes is detected, and the humidity in the environment is measured according thereto.

In the fabrication method of the present invention, a $SiO_2$ layer is formed on a semiconductor substrate as a sensing film. Two comb-type trenches, each with a plurality of teeth, are formed on the $SiO_2$ layer and a conductive material is filled into the two comb-type trenches to form two comb-type electrodes.

The present invention also provides a method for detecting humidity in a predetermined environment. In the detection method, a humidity sensor is provided in the predetermined environment for a predetermined time, wherein the humidity sensor has a substrate, two comb-type electrodes deposed on the substrate, each having a plurality of teeth, and a $SiO_2$ sensing film between the teeth of the two comb-type electrodes on the substrate. A predetermined voltage difference is then applied between the two comb-type electrodes, and a leakage current between the two comb-type electrodes is determined. Finally, the humidity in the predetermined environment is determined according to the leakage current.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
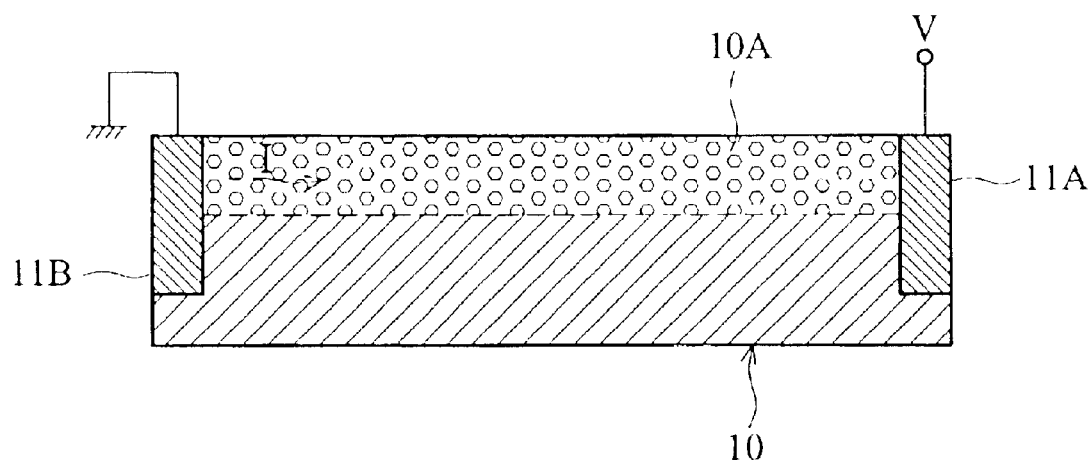
FIG. 1 illustrates the sensing principle of a humidity sensor according to the present invention.
Figure 2:
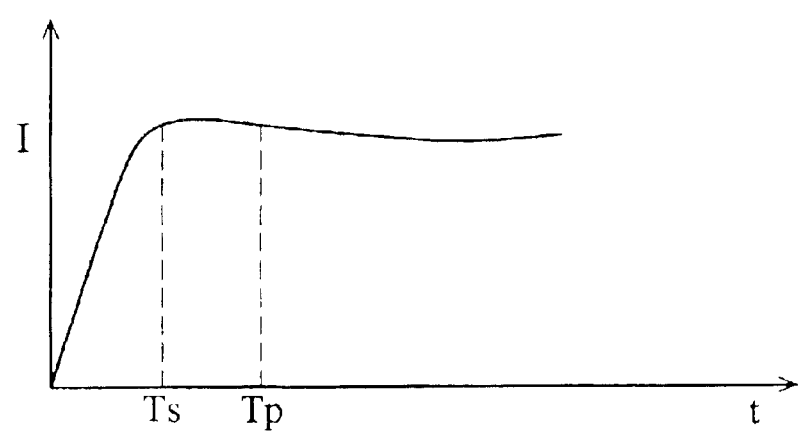
FIG. 2 shows the relationship between time and leakage current when a $SiO_2$ film is exposed to the environment.

The present invention senses the humidity in an environment by $SiO_2$ sensing film and the sensing principle thereof is Illustrated and referenced in FIG. 1 and FIG. 2. FIG. 1 is a diagram of the humidity sensor according to the present invention. FIG. 2 shows the relationship between time and leakage current when a $SiO_2$ film is exposed to the environment. As shown in FIG. 1, when a $SiO_2$ film 10 is disposed in a detecting environment, the surface layer 10A of the $SiO_2$ film absorbs the humidity. Consequently, the charge density In the surface layer 10A of the $SiO_2$ film changes the surface layer 10A to a conductive layer from an isolation layer. Thus, a leakage current can be measured by applying a voltage difference between the electrodes 11A and 11B. As shown In FIG. 2, the surface layer 10A has absorbed humidity and is saturated after time Ts, and the leakage current between the electrodes trends to be constant. Thus, the humidity concentration in the detected environment is obtained according to the leakage current between the electrodes 11A and 11B after time Tp.

Figure 3:
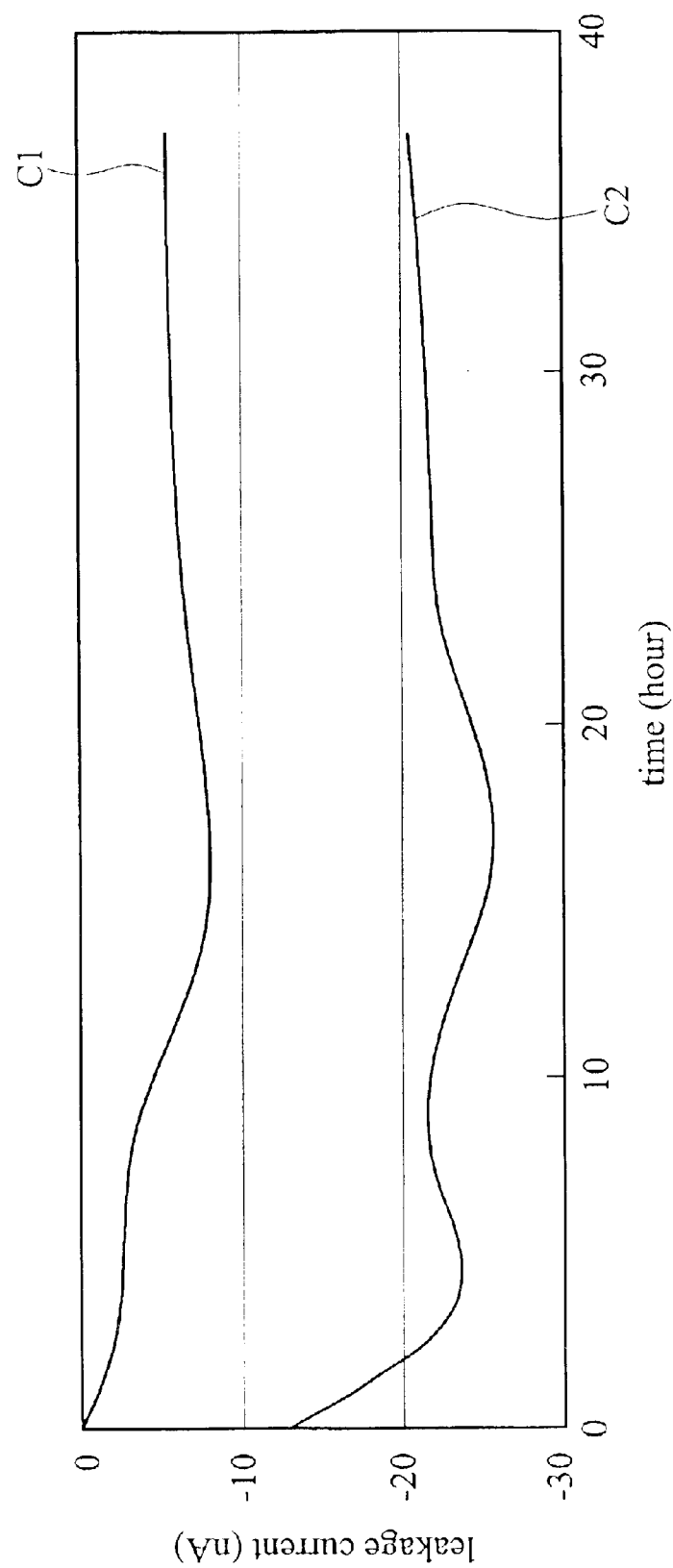
FIG. 3 shows the relationship between time and leakage current when a $SiO_2$ film is exposed in a box.

FIG. 3 shows the relationship between time and leakage current when a $SiO_2$ film is exposed to the atmosphere in a box, respectively. In FIG. 3, the curve $C_1$ shows the relationship between time and leakage current when a $SiO_2$ film is exposed in a box, and the curve $C_2$ shows the relationship between time and leakage current when a $SiO_2$ film is exposed to the atmosphere. Thus, the leakage current between the electrodes 11A and 11B in atmosphere is larger than that in the box when applying a voltage difference between the two electrodes.

FIGS. 4a~4d are cross-sections of the fabrication method according to the present invention, and FIGS. 5a~5d are plane views of FIGS. 4a~4d.

Figure 4A:
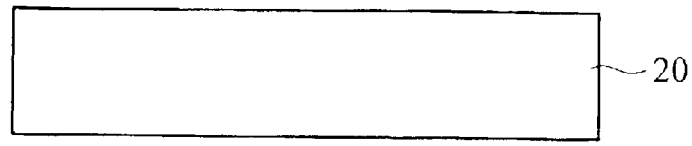
FIGS. 4a~4d are cross-sections of the fabrication method according to the present invention.
Figure 4B:
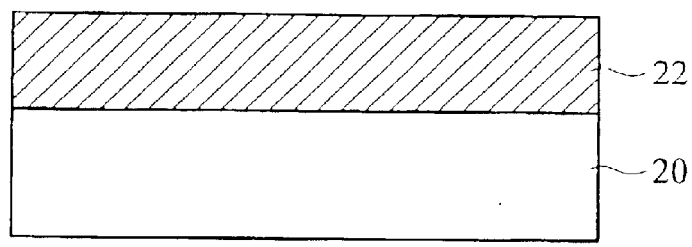
Figure 5A:
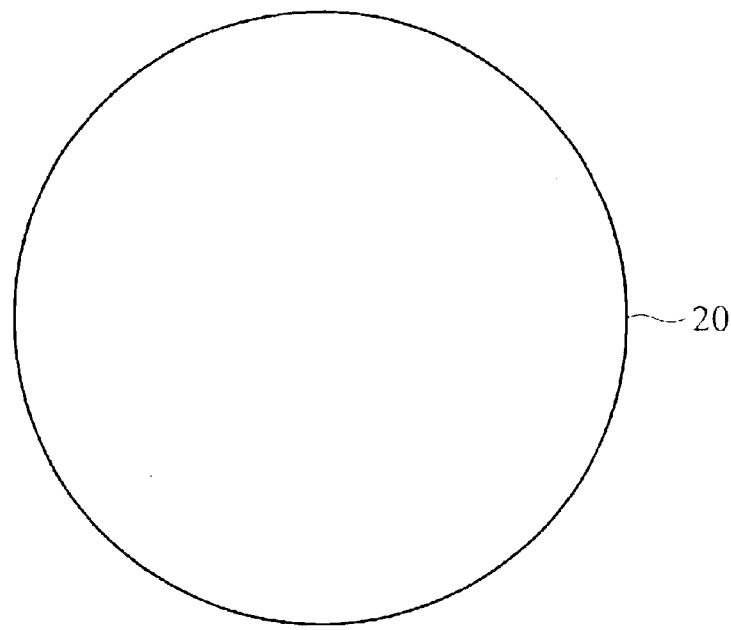
FIGS. 5a~5d are plane views of FIGS. 4a~4d.
Figure 5B:
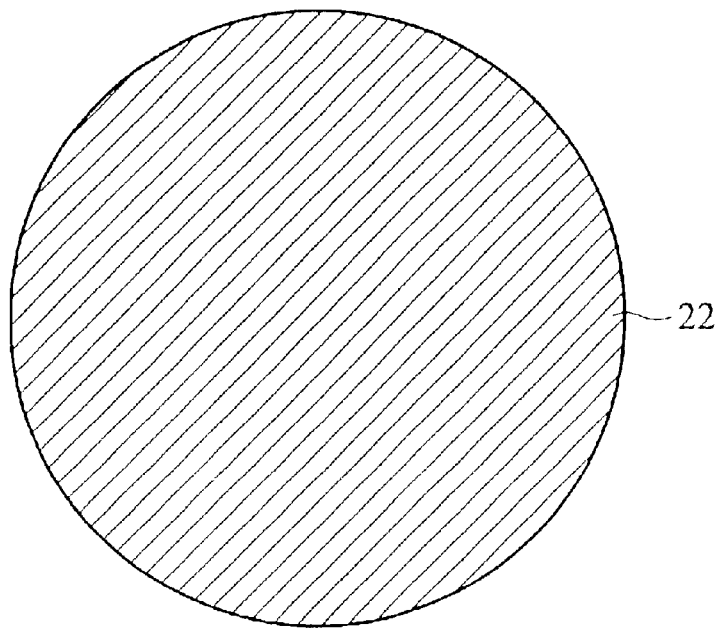

As shown in FIGS. 4a and 5a, a semiconductor substrate 20 is provided. As shown in FIGS. 4b and 5b, a $SiO_2$ sensing film 22 is formed on the semiconductor substrate 20 by chemical vapor deposition (CVD) using tetraethyl orthosilicate (TEOS) and $O_3$ as process gases. Alternately, the $SiO_2$ sensing film 22 may be formed on the semiconductor substrate 20 by thermal oxidation.

Figure 4C:
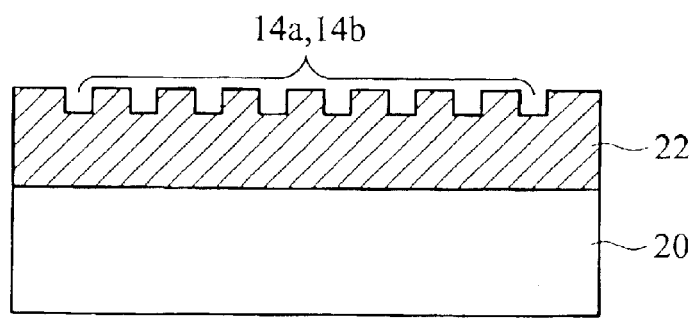
Figure 5C:
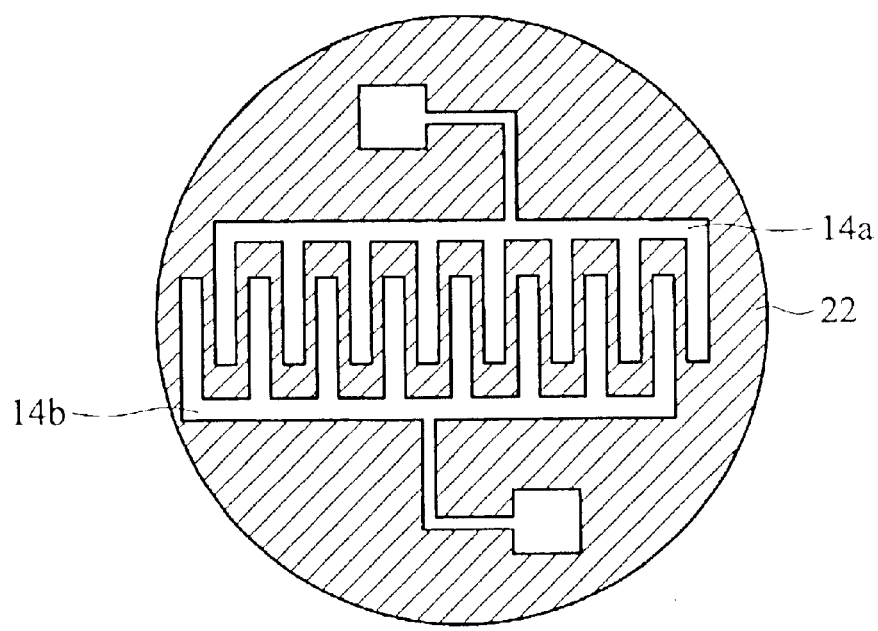

As shown in FIGS. 4c and 5c, two comb-type trenches 14a and 14b are formed in the $SiO_2$ sensing film 22 by photolithography and etching, wherein each comb-type trench has a plurality of teeth with each tooth a predetermined distance, for example 0.175 micrometers, from adjacent teeth.

Figure 4D:
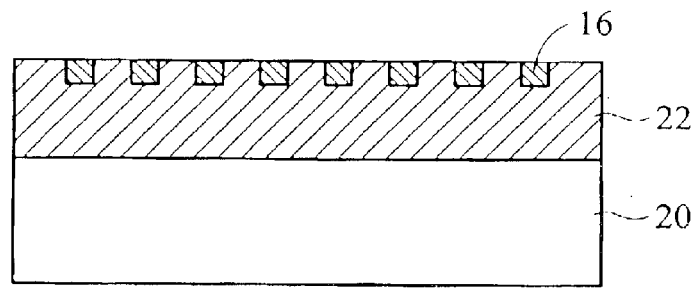
Figure 5D:
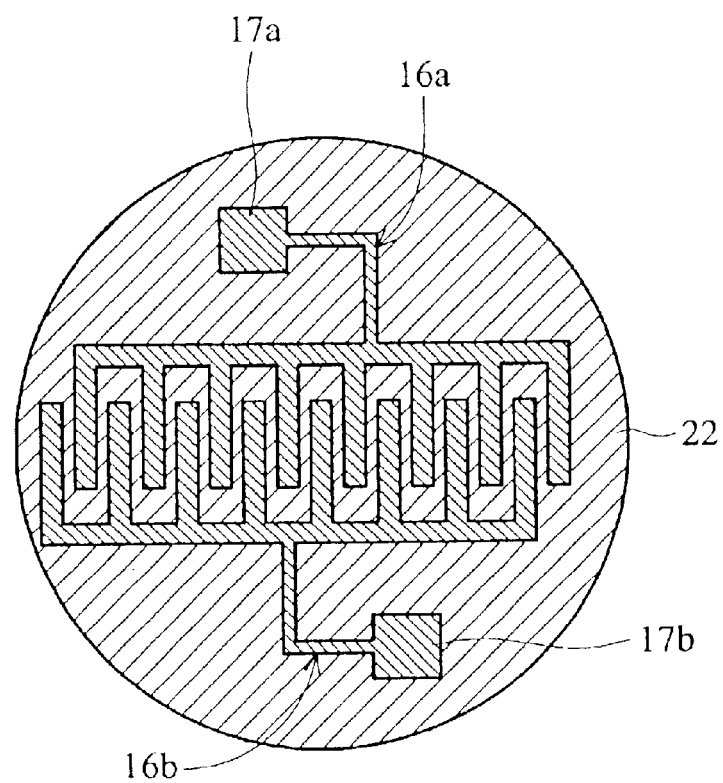

In FIGS. 4d and 5d, a conductive material 16 is filled into the two comb-type trenches 14a and 14b to form two comb-type electrodes 16a and 16b. In the present invention, the two electrodes 16a and 16b are made of conductive material, such as polysilicon material or metallic material, for example Au, Cu, Ag, Al, W and the like. The conductive material is filled into the trenches 14a and 14b and on the whole surface of the semiconductor substrate 20 by deposition or sputtering. The conductive material outside the trenches 14a and 14b is then removed by chemical mechanical polishing. Each of the two comb-type electrodes 16a and 16b has a pad (17a and 17b) coupled to a voltage source, and a plurality of teeth. Each tooth of the comb-type electrodes 16a and 16b is a distance, such as 0.175 micrometers, from the adjacent teeth, such that the opposing teeth of the comb-type electrodes 16a end 16b alternate.

Figure 6:
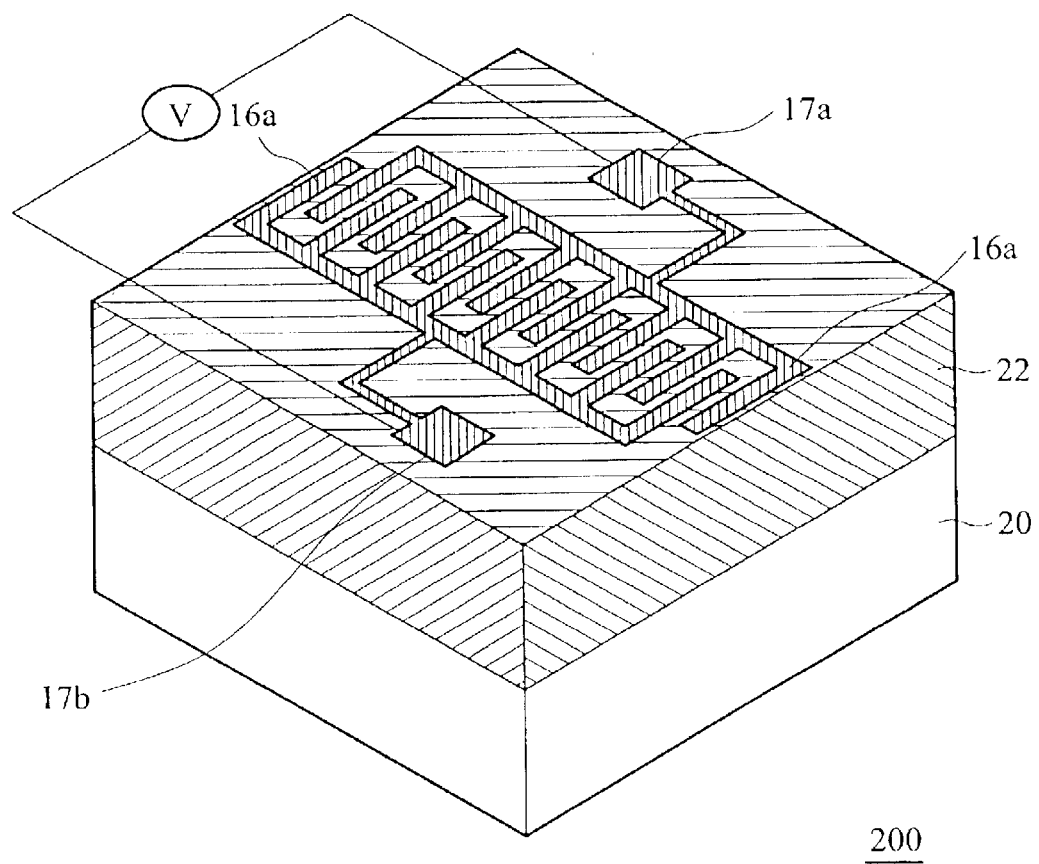
FIG. 6 is a diagram for the detection method of the present invention.

FIG. 6 shows the humidity sensor 200 of the present invention, in which two comb-type electrodes 16a and 16b are formed on a semiconductor substrate 20, each having a pad (17a and 17b) coupled to a voltage source and a plurality of teeth. Each tooth of the comb-type electrodes 16a and 16b is a distance, such as 0.175 micrometers, from the adjacent teeth, such that the opposing teeth of the comb-type electrodes 16a and 16b alternate. A $SiO_2$ sensing film is formed between the two electrodes 16a and 16b and on the surface of the semiconductor substrate 20. When an appropriate voltage difference is applied between the two comb-type electrodes 16a and 16b, a leakage current therebetween is obtained.

The present invention also provides a method for detecting humidity in a detecting environment. In the detection method, a humidity sensor 200 as shown in FIG. 6 is provided, with a relational table between the leakage current and corresponding humidity levels previously established. The relational table is established by measuring leakage current between the comb-type electrodes under varying humidity levels.

The humidity sensor 200 is then disposed in a detecting environment for a predetermined time. A processing unit (not shown) then applies a predetermined voltage difference, for example 1.8V, between the two comb-type electrodes 16a and 16b, and detects the leakage current therebetween.

Finally, the humidity of the detecting environment is obtained according to the detected leakage current and the relational table.

Thus, the present invention can detect the humidity in a detecting environment.

Figure 7:
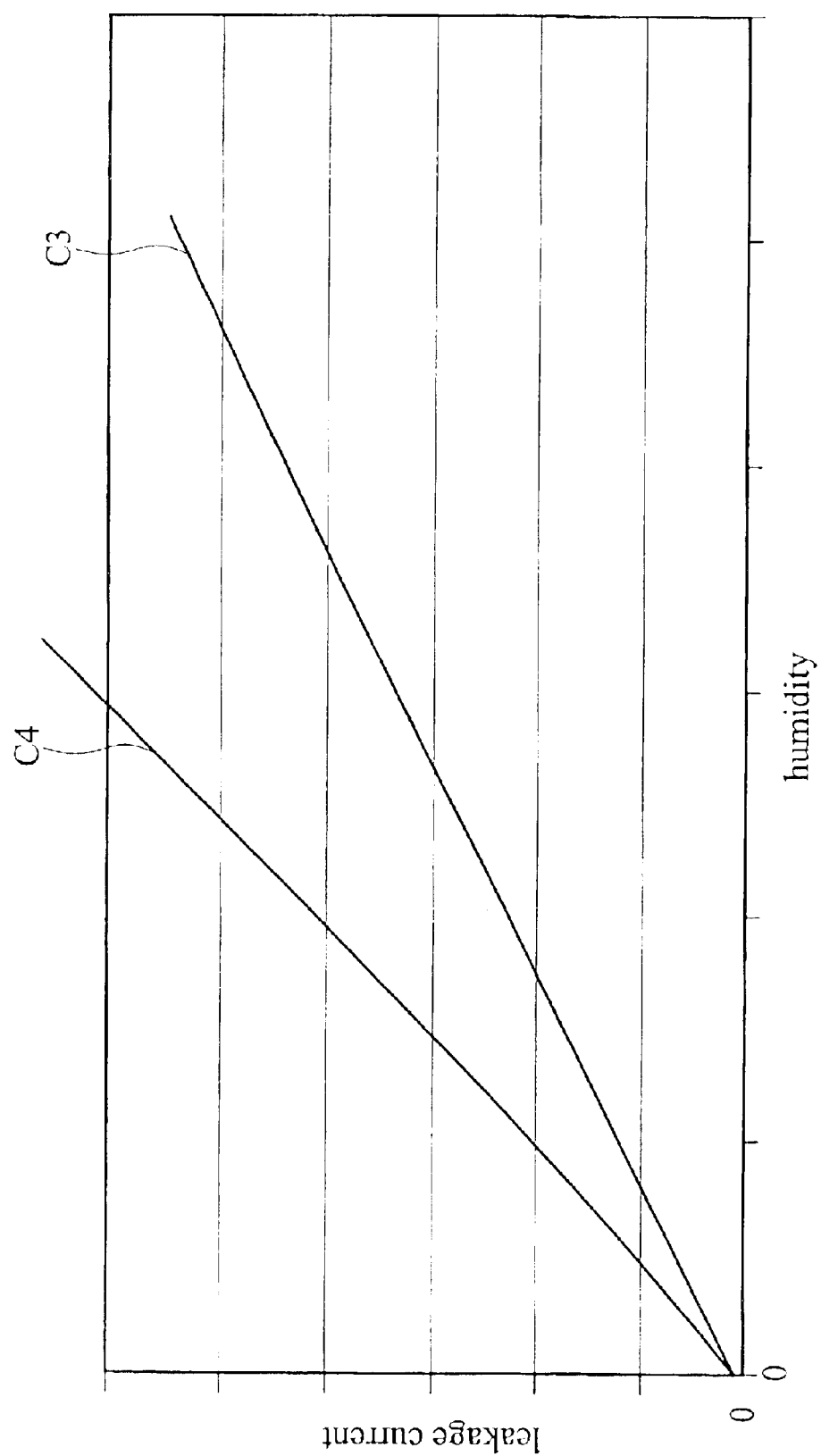
FIG. 7 shows the relationship between the leakage current and humidity when spacing between teeth of the comb-type electrodes is varied.

In addition, FIG. 7 shows the relationship between humidity and leakage current between the comb-type electrodes with varying teeth spacing. In FIG. 7, the curve $C_3$ shows the relationship between humidity and leakage current when the space between the teeth of the comb-type electrode is 0.175 micrometers, and the curve $C_4$ shows the relationship between humidity and leakage current when the space between the teeth of the comb-type electrode is less than 0.1 micrometer. As shown in FIG. 7, the humidity sensor has increased sensitivity as the space between teeth of the comb-type electrodes decreases. Therefore, as semiconductor technology advances, the space between teeth of the comb-type electrodes decreases, enhancing sensitivity of the humidity sensor.

Furthermore, the humidity absorbed into the $SiO_2$ sensing film can be removed by heating for a time, such that the humidity sensor can be reused to detect humidity in another environment. The humidity sensor can also be coupled to peripheral circuits and formed on a semiconductor chip for applications, such as air conditioning systems, dehumidifiers, dryers, and the like.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A humidity sensor, comprising:

a substrate;

two comb-type electrodes disposed on the substrate, each having a plurality of teeth spaced apart from adjacent teeth by 0.175 micrometers; and a $SiO_2$ sensing film disposed between the teeth of the two comb-type electrodes on the substrate, wherein a processing unit applies a predetermined voltage between the two comb-type electrodes, detects a leakage current therebetween, and determines the humidity in the environment according thereto.

2. The humidity sensor as claimed in claim 1, wherein the two comb-type electrodes are made of metal.

3. The humidity sensor as claimed in claim 1, wherein the two comb-type electrodes are made of polysilicon.

4. The humidity sensor as claimed in claim 1, wherein each comb-type electrode has a pad thereon.

5. The humidity sensor as claimed in claim 1, wherein the opposing teeth of the two comb-type electrodes alternate.

6. A method of fabricating a humidity sensor, comprising:

providing a substrate;

forming a $SiO_2$ layer on the substrate as a sensing film;

forming two comb-type trenches each with a plurality of teeth on the $SiO_2$ layer; and filling a conductive material into the two comb-type trenches to form two comb-type electrodes.

7. The method as claimed in claim 6, wherein the conductive material is metallic.

8. The method as claimed in claim 6, wherein the conductive material is polysilicon.

9. The method as claimed in claim 6, further comprising a step of forming two pads on the comb-type electrodes respectively, wherein the $SiO_2$ layer is formed by chemical vapor deposition with TEOS and $O_3$.

10. A method for detecting humidity in a predetermined environment; comprising:

providing a humidity sensor in the predetermined environment for a predetermined time, wherein the humidity sensor has a substrate, two comb-type electrodes deposed on the substrate, each having a plurality of teeth, and a $SiO_2$ sensing film between the teeth of the two comb-type electrodes on the substrate;

applying a predetermined voltage difference between the two comb-type electrodes, wherein the predetermined voltage difference is about 1.8 V;

detecting a leakage current between the two comb-type electrodes; and determining the humidity in the predetermined environment according to the leakage current.

11. The method as claimed in claim 10, wherein the humidity in the predetermined environment is determined by a relational table between leakage current and humidity.

* * * * *